(12) United States Patent
Li et al.

(10) Patent No.: US 9,534,214 B2
(45) Date of Patent: *Jan. 3, 2017

(54) SUBSTRATES AND ASSOCIATED METHODS FOR ELUTION OF NUCLEIC ACIDS

(71) Applicant: General Electric Company, Schenectady, NY (US)

(72) Inventors: Bing Li, Clifton park, NY (US); Gregory Andrew Grossmann, Halfmoon, NY (US); Erik Leeming Kvam, Niskayuna, NY (US); Brian Christopher Bales, Niskayuna, NY (US); Jason Louis Davis, Albany, NY (US)

(73) Assignee: General Electric Company, Niskayuna, NY (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/068,633

(22) Filed: Oct. 31, 2013

(65) Prior Publication Data

US 2015/0119566 A1    Apr. 30, 2015

(51) Int. Cl.
*C12N 15/10* (2006.01)
*B01J 20/22* (2006.01)
*B01J 20/26* (2006.01)

(52) U.S. Cl.
CPC ............ *C12N 15/1006* (2013.01); *B01J 20/22* (2013.01); *B01J 20/261* (2013.01)

(58) Field of Classification Search
CPC ..... C12N 15/1006; B01J 20/22; B01J 20/2061
USPC .................. 536/23.1, 25.42; 502/7
See application file for complete search history.

(56) References Cited

U.S. PATENT DOCUMENTS

| | | | |
|---|---|---|---|
| 5,756,126 A | 5/1998 | Burgoyne | |
| 6,184,011 B1 | 2/2001 | Siegel et al. | |
| 7,589,184 B2 | 9/2009 | Hogan et al. | |
| 2001/0007746 A1 | 7/2001 | Smith et al. | |
| 2002/0146696 A1* | 10/2002 | Burgoyne | C12N 15/1006 435/6.1 |
| 2004/0101895 A1 | 5/2004 | Fomovskaia et al. | |
| 2004/0235034 A1 | 11/2004 | Kuno et al. | |
| 2005/0009045 A1 | 1/2005 | Greenfield et al. | |
| 2005/0123965 A1* | 6/2005 | Yamashita | C12N 15/101 435/6.16 |
| 2008/0176209 A1 | 7/2008 | Muller et al. | |
| 2009/0043087 A1 | 2/2009 | Davis et al. | |
| 2010/0178210 A1 | 7/2010 | Hogan et al. | |
| 2011/0059869 A1 | 3/2011 | Kojima et al. | |
| 2011/0081363 A1* | 4/2011 | Whitney | A01N 1/00 424/184.1 |
| 2012/0289690 A1 | 11/2012 | Page et al. | |
| 2013/0102501 A1 | 4/2013 | Craighead et al. | |

FOREIGN PATENT DOCUMENTS

| | | | | |
|---|---|---|---|---|
| WO | WO 91/18091 | * | 11/1991 | ............... C12N 9/96 |
| WO | WO 2010/144682 | * | 12/2010 | ............... C12N 9/96 |
| WO | 2011080160 A1 | | 7/2011 | |
| WO | WO 2011/131720 A1 | * | 10/2011 | ............... C12N 9/64 |
| WO | 2012113907 A2 | | 8/2012 | |

OTHER PUBLICATIONS

Wolfgramm et al., "Simplified Buccal DNA Extraction with FTA Elute Cards", Forensic Science International: Genetics, vol. No. 3, Issue No. 2, pp. 125-127, Mar. 1, 2009.

Johanson et al., "DNA Elution from Buccal Cells Stored on Whatman FTA Classic Cards using a Modified Methanol Fixation Method", Biotechniques, vol. No. 46, Issue No. 4, pp. 309-311, Apr. 2009.

Miles et al., "Improved Elution of DNA from Whatman FTA Cards Using PrepGEM/ ForensicGEM Storage Card Extraction Kits", ZyGEM, Oct. 1, 2012.

Henniges et al., "Electron Beam Irradiation of Cellulosic Materials—Opportunities and Limitations", Materials, vol. No. 6, pp. 1584-1598, Apr. 29, 2013.

International Search Report and Written Opinion issued in connection with corresponding Application No. PCT/US2014/062570 on Jul. 10, 2015.

* cited by examiner

*Primary Examiner* — Ganapathy Krishnan
(74) *Attorney, Agent, or Firm* — Eileen B. Gallagher

(57) ABSTRACT

A solid substrate for biological sample storage under dry-state and elution of biomolecules is provided. The dry, solid substrate is coated with saccharides, such as monosaccharides, oligosaccharides, polysaccharides or combinations thereof, and the substrate is comprised of one or more protein denaturing agents impregnated therein under a substantially dry state. A method for elution of biomolecules from biological samples is also provided. The compositions disclosed herein provide for enhanced elution and recovery of biomolecules, such as nucleic acids, from the sample. The sample is disposed on a substrate, dried to a substantially dry state; eluted from the biological sample dried on the substrate by rehydrating the substrate in an elution buffer.

14 Claims, 2 Drawing Sheets

SUBSTRATES AND ASSOCIATED METHODS FOR ELUTION OF NUCLEIC ACIDS

FEDERALLY SPONSORED RESEARCH & DEVELOPMENT

This invention was made with Government support under contract number (HR0011-11-C0127) awarded by the Defense Advanced Research Projects Agency. The Government has certain rights in the invention.

FIELD

The invention generally relates to modified substrates for the stabilization and effective elution of nucleic acids from dried biological samples. Methods for stabilization and elution of nucleic acids from a biological sample in a dry format are also described.

BACKGROUND

Dry-state biological sample storage and preservation is desired for various applications, such as analyte detection, sensing, forensic and diagnostic applications, genome sequencing, whole-genome amplification, and the like. Long-term storage, transport and archiving of bio-specimens on filter paper and other chemically modified matrices are well-known techniques for preserving different biomolecules, such as nucleic acids, peptides, and proteins for different downstream applications.

Existing methods for the extraction of biomolecules from a substrate generally employ the use of different types of aqueous and organic extraction solvents, which may have adverse effects on biomolecule stability or downstream usability. Methods are known for using temperature and pH for differential binding and selective release of biomolecules, such as nucleic acids, from a solid substrate, for example, by binding of nucleic acids at acidic pH and release at alkaline pH. Alternatively, very high temperature or alkaline pH or combinations of both may be used to release bound biomolecules from a substrate through denaturation. The mixed mode resins are also known for recovering a target compound from aqueous solution at high or low ionic strength, using change in pH. The use of extremes of various environmental factors, such as pH, temperature, and/or high salt concentrations for re-dissolving or eluting nucleic acids may cause nucleic acids, especially RNA, to denature or degrade. Other environmental factors, such as, pressure, chemical or enzymatic hydrolysis, or the presence of contaminants may also promote the degradation of archived biomolecules such as DNA, RNA, or proteins during collection and storage.

Furthermore, known techniques for eluting of biomolecules from solid substrates may result in comparatively low recovery. For example, the recovery of purified nucleic acids from solid substrates may be low or inefficient as determined by quantitative real time polymerase chain reaction (PCR). The success of the downstream applications of isolated nucleic acids from a sample may also depend on maintaining the integral structure and function of target biomolecules and the amount of biomolecules used for each application.

Accordingly, a simplified method and an appropriate solid substrate for collecting, storing and eluting biomolecules from a sample disposed on the substrate with greater recovery is needed. In addition, maintaining the structural and functional integrity of the eluted nucleic acids is highly desirable.

BRIEF DESCRIPTION

In one embodiment, a solid substrate for biological sample storage and elution comprises one or more monosaccharides, oligosaccharides, polysaccharides or combinations thereof, and one or more protein denaturing agents impregnated therein the substrate in a substantially dry state.

In another embodiment, a method for eluting biomolecules from a biological sample disposed on a saccharide-coated solid substrate, comprises contacting the biological sample to the substrate, wherein the substrate comprises one or more monosaccharides, oligosaccharides, polysaccharides or combinations thereof on a surface of the substrate, and one or more protein denaturing agents impregnated therein; drying the biological sample to a substantially dry state; eluting the biomolecules from the biological sample dried on the substrate by rehydrating the substrate in an elution buffer.

In yet another embodiment, a method for elution of nucleic acids from a biological sample disposed on a saccharide-coated, solid and dry cellulose substrate, comprises contacting the biological material to the substrate comprising one or more of melezitose, raffinose, dextran or combinations thereof, and one or more thiocyanate salts impregnated therein; drying the biological sample to a substantially dry state; and eluting the nucleic acid from dried biological sample by rehydrating the substrate in an elution buffer.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
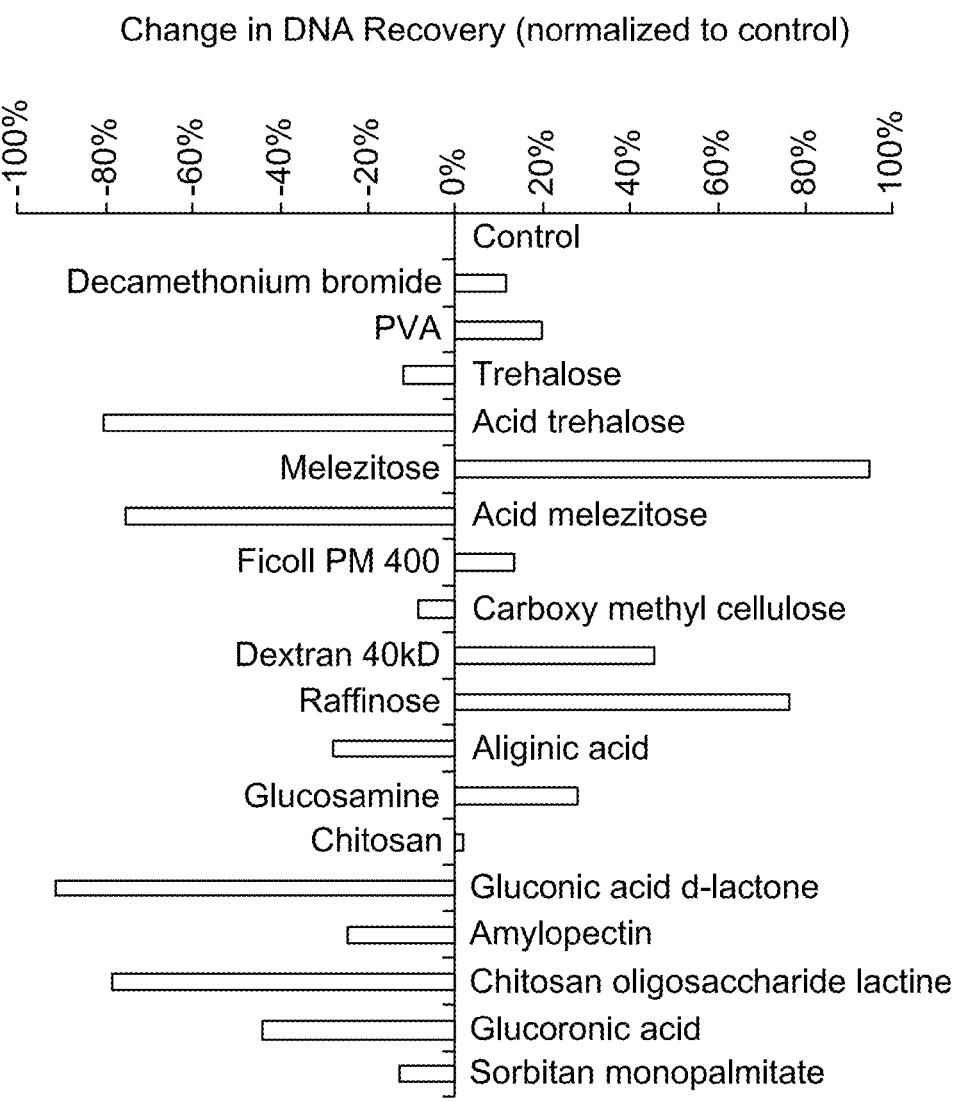
FIG. 1 is a graph comparing DNA recovery from different dip-coated cellulose substrates relative to a control formulation comprising FTA™ Elute.

The embodiments of the invention provide suitable matrices and methods for elution of nucleic acids, such as DNA. One or more embodiments of the invention relate to a nucleic acid extraction substrate, wherein the substrate is configured to collect, extract and store nucleic acids from a biological sample for a prolonged period within a single process step, followed by elution of the nucleic acids for use in various downstream applications. The substrate is configured to store nucleic acids in a substantially dry-state at ambient temperature and to elute the stored nucleic acids while preserving the integrity of the nucleic acids.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "nucleic acid" as referred to herein comprises all forms of DNA (e.g. genomic DNA, mtDNA) or RNA (e.g., mRNA, miRNA, rRNA, tRNA, piRNA, ncRNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using the extraction methods disclosed. "Fragment" refers to a portion of a nucleic acid (e.g., RNA or DNA).

The term, "reducing agents" as referred to herein include any chemical species that provides electrons to another chemical species. A variety of reducing agents are known in the art. Exemplary reducing agents include dithiothreitol (DTT), 2-mercaptoethanol (2-ME), and tris(2-carboxyethyl) phosphine (TCEP). Moreover, any combination of these or other reducing agents may be used. In particular embodiments, the reducing agent is TCEP.

The term "buffer" as used herein includes, for example, 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), and phosphate buffers. This list of potential buffers is for illustrative purposes only. The pH of the buffer selected for use in the compositions and methods disclosed herein is typically acid-titrated in the range of 2 to 7.

One or more embodiments of a solid substrate for biological sample storage and elution are provided. In some embodiments, the solid substrate for eluting biomolecules from a biological sample, comprises one or more monosaccharides, oligosaccharides, polysaccharides or combinations thereof on a surface of the substrate, and one or more protein denaturing agents impregnated therein the substrate under a dry state.

As noted, the solid substrates used for storage and elution of nucleic acids comprise one or more monosaccharides, oligosaccharides, polysaccharides or combinations thereof on a surface of the substrate, wherein the term "substrate" is interchangeably used herein as "solid substrate" or "saccharide coated substrate". As defined, the "saccharide coated substrate" also comprises protein denaturing agents impregnated therein. The saccharide coated substrate comprises saccharides or protein denaturing agents under dry condition. The term "solid substrate" as used herein refers to a non-water dissolvable material, which enables collection, extraction and storage of nucleic acids followed by elution without solubilizing the solid substrate.

The solid substrate includes, but is not limited to, materials such as cellulose, cellulose acetate, nitrocellulose, glass fibers or combinations thereof. In one embodiment, the substrate comprises cellulose. In one or more embodiments, the substrate is selected from a nitrocellulose membrane, a cellulose membrane, a cellulose acetate membrane, a regenerated cellulose membrane, a nitrocellulose mixed ester membranes, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, and any combination of two or more of the above membranes.

In some embodiments, the substrate is a porous cellulose membrane. In one embodiment, the solid substrate is a porous cellulose paper, such as a cellulose substrate from Whatman™. In one example, the cellulose substrate from Whatman™ comprises 903-cellulose, FTA™ or FTA™ Elute.

As noted, the solid substrates used for storage and elution of nucleic acids comprise one or more monosaccharides, oligosaccharides, polysaccharides or combinations thereof in the substrate, wherein the saccharides are disposed on the substrate and then dried to a substantially dry state, thereby creating a rehydratable composition. In some embodiments, a coating of the saccharide is disposed over the substrate-surface, wherein the incorporation of the sugar moieties into the substrate may be achieved by the "dipping" or "dip-coating" procedure described below. In some embodiments, the substrate comprises one or more monosaccharides, oligosaccharides, polysaccharides or combinations thereof, which may be developed by dipping the substrate into one or more saccharide solutions followed by drying. The saccharide coating on the substrate may be developed using any standard method for coating a substrate known in the art. In some embodiments, such methods accomplish incorporation of the composition into the dry solid substrate. Following incorporation of the composition into the dry solid substrate, the solid substrate is dried using any appropriate method.

In one embodiment, the substrate is treated with a saccharide, such as L- or D-form of the sugar, including monosaccharides, polysaccharides or oligosaccharides, to provide improved elution of nucleic acids from the saccharide-coated substrate. Different saccharides including monosaccharides, oligosaccharides and polysaccharides, which are used for coating the substrate, are defined herein. The term "monosaccharide" is referred to herein, as a compound having a single carbohydrate unit, generally known as a sugar. The monosaccharide may be selected from glucosamine, glucose, fructose, galactose, galactosamine, xylose, ribose, sialic acid, N-acetylglucosamine or a combination thereof.

The term "oligosaccharide" is referred to herein, as a compound which upon hydrolysis produces three to ten units of carbohydrates. In some embodiments, the substrate comprises oligosaccharides, wherein the oligosaccharide is selected from melezitose, raffinose, maltotriulose, ketose or combination thereof. In one embodiment, the substrate comprises an oligosaccharide, wherein the oligosaccharide is melezitose. In another embodiment, the substrate comprises an oligosaccharide, wherein the oligosaccharide is raffinose. Trisaccharides are oligosaccharides of 3 monosaccharide units; polysaccharides are longer chains of monosaccharides. In these embodiments, the oligosaccharides exclude disaccharides, which are composed of two monosaccharide units, such as trehalose.

The term, "polysaccharide" is referred to herein as a compound comprising more than ten carbohydrate units, upon hydrolysis, each of the polysaccharides produces more than ten units of carbohydrates. In some embodiments, the substrate comprises polysaccharides, wherein the polysaccharide is selected from the group comprising dextran, ficoll, chitosan, amylopectin, alginate, carboxymethyl cellulose, or combinations thereof, wherein the polysaccharide of the present invention excludes inulin.

In one or more embodiments, the solid substrate further comprises one or more protein denaturing agents (or protein denaturing agents) in addition to the saccharide-coating under a dry state. In other embodiments, the saccharide-coated solid substrate comprises buffer reagents, reducing agents, and optionally free-radical scavengers in addition to protein denaturing agents in a dry state. The substrate may extract and preserve nucleic acids under dry conditions, wherein the dried nucleic acids may further be eluted from the substrate by re-hydrating with water or aqueous buffer. Use of a dry solid substrate for collecting, extracting, preserving and eluting a sample maintains the concentration of available analyses and reduces the issues related to sample degradation, wherein the intact nucleic acids may be eluted with greater ease from the saccharide coated substrate.

As noted, in some embodiments, one or more protein denaturing agents are impregnated within the substrate under a substantially dry state. As used herein, the term "substantially dry state" refers to further drying the sample to have approximately less than 2% of water content. In one or more embodiments, the substrate comprises a protein denaturing agent. In some embodiments, the protein denaturing agent comprises salts, detergents, chaotropes, amino acids or combinations thereof. Without intending to be limited to a particular protein denaturing agent, exemplary protein denaturing agents include guanidinium thiocyanate, guanidinium hydrochloride, sodium thiocyanate, potassium thiocyanate, arginine, sodium dodecyl sulfate (SDS), urea or a combination thereof. In some embodiments, the substrate comprises a protein denaturing agent that is selected from thiocyanate salts impregnated in a dry state. Exemplary thiocyanate salts include, but are not limited to, guanidinium thiocyanate, sodium thiocyanate, potassium thiocyanate or combinations thereof. In one embodiment, the substrate comprises guanidium thiocyanate as a protein denaturing agent.

The protein denaturing agent may further comprise a chaotrope or a detergent. Without intending to be limited to a particular denaturing agent, protein denaturing agents may be categorized as either weak denaturing agents or strong denaturing agents depending on their biophysical properties and ability to completely inhibit biological enzyme activity. In some embodiments, weak protein denaturing agents (e.g. detergent) may be used for lysing cells and disrupting protein-protein interactions without denaturing nucleic acids. In further embodiments, use of strong protein denaturing agents (e.g. chaotrope) may also denature nucleic acid secondary structure in addition to denaturing cells and proteins. Numerous protein denaturing agents are known in the art and may be selected for use in the compositions and methods described herein.

Exemplary detergents may be categorized as ionic detergents, non-ionic detergents, or zwitterionic detergents. The ionic detergent may comprise anionic detergent such as, sodium dodecylsulphate (SDS) or cationic detergent, such as ethyl trimethyl ammonium bromide. Non-limiting examples of non-ionic detergent for cell lysis include TritonX-100, NP-40, Brij 35, Tween 20, Octyl glucoside, Octyl thioglucoside or digitonin Some zwitterionic detergents may comprise 3-[(3-Cholamidopropyl)dimethylammonio]-1-propanesulfonate (CHAPS) and 3-[(3-Cholamidopropyl) dimethylammonio]-2-hydroxy-1-propanesulfonate (CHAPSO). In some other embodiments, the protein denaturing agent may be selected from guanidinium hydrochloride, arginine, sodium dodecyl sulfate (SDS), urea, or combinations thereof. In some embodiments, the impregnated reagents comprise lytic reagents, nucleic acid-stabilizing reagents, nucleic acid storage chemicals and combinations thereof.

The substrate may further comprise a reducing agent, a buffer or combinations thereof impregnated therein under a dry state. The reducing agent may include dithiothreitol (DTT), 2-mercaptoethanol (2-ME), tris(2-carboxyethyl) phosphine (TCEP) or combinations thereof.

As noted, the substrate further comprises a buffer, wherein the buffer may be selected from 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers or combinations thereof.

As noted, the solid substrate for biological sample storage and elution refers that the solid substrate is configured for biological sample storage and elution. The term "configured for" is referred to herein as the structure or composition of the substrate that enables the substrate to collect, extract, and store nucleic acids followed by elution. The terms "storage" is used herein with respect to maintaining the extracted nucleic acids in a format suitable for further analysis.

In some embodiments, the solid substrate for biological sample storage and elution is a solid phase extraction substrate, which is coated with a formulation comprising saccharides. A substrate, where the solid phase extraction method is used, is referred to herein as a solid phase extraction substrate. Solid-phase extraction (SPE) technology has been leveraged to reduce the extraction times of high purity nucleic acids for sequencing and other applications. The solid phase extraction is an extraction method that uses a solid phase and a liquid phase to isolate one or more molecules of the same type, or different types, from a material. The solid phase extraction substrate is used, for example, to purify a sample upstream of a chromatographic or other analytical method. One example of the method comprises loading a sample (e.g. a biological sample) onto the saccharide coated solid phase extraction substrate, storing the substrate at ambient temperature to achieve a substantially dry state, and rehydrating the substrate with a suitable buffer to elute nucleic acids from the substrate.

In some embodiments, the substrate is configured to improve the recovery of biomolecules. The coating composition of the present invention provides enhanced release and recovery of nucleic acids during an elution process, as shown in FIG. 1. The saccharide-coated substrate for releasing nucleic acid is especially useful during elution of nucleic acids from a less quantity of sample disposed on the substrate. The elution of nucleic acids from a saccharide-coated substrate avoids the need to use high ionic strength or alkaline pH buffers for elution and subsequent dilution of the eluted nucleic acids to adjust the ionic strength and pH required for the downstream applications. As a consequence, any loss of nucleic acids through further sample-dilution or reduced recovery due to degradation, denaturation or dilution of small amounts of nucleic acid may be avoided. Use of a saccharide-coated substrate is advantageous when the nucleic acid of interest is present in a sample at a low copy number and for use with certain detection and/or amplification methods, wherein the saccharide-coated substrate enables elution of nucleic acids with greater ease and high yield.

Figure 2:
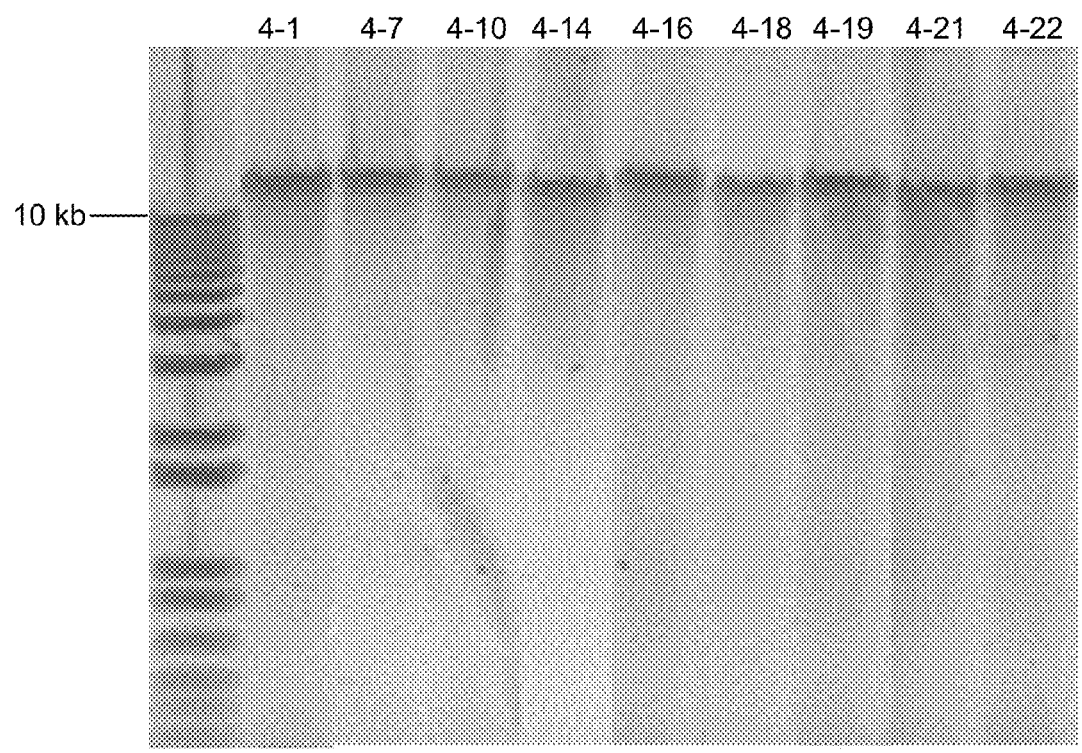
FIG. 2 is an image of an agarose gel electrophoresis showing recovery of high molecular weight (intact) DNA from the substrates of one embodiment of the invention.

In some embodiments, the substrate is configured to elute biomolecules in intact forms. As noted, the saccharide coated substrate further enhances the recovery of intact nucleic acids, wherein the term "intact" refers to non-degraded or substantially non-degraded forms of the nucleic acids. For example, high molecular weight nucleic acids are recovered from a sample disposed on the saccharide coated substrate, as shown in FIG. 2. The substrate ensures prevention of degradation of the nucleic acids during collection, storage or elution.

In some embodiments, the saccharide-coated substrate reduces the risk of leaching chemicals from a chemically modified substrate or ionizable groups with the eluted nucleic acids, which can otherwise lead to significant problems, specifically if the resultant product is used in polymerase chain reaction (PCR). The presence of saccharides in the eluted nucleic acid fraction does not interfere with PCR.

In some embodiments, the dried reagents impregnated in the substrate are hydrated by adding a buffer, water or a biological sample. In some embodiments, water or buffer is added to hydrate the substrate and reconstitute or activate the reagents embedded in the substrate. In some embodiments, the hydration of the substrate may result in reconstituting the reagents impregnated in the substrate.

In one embodiment, the substrate is impregnated with nucleic acid stabilizing reagents. These stabilizing reagents may include DNAse or RNAse inhibitors, buffer reagents, or chelating agents. As noted, the substrate further comprises a chelating agent, wherein the chelating agent is selected from ethylenediaminetetraacetic acid (EDTA), citric acid, ethylene glycol tetraacetic acid (EGTA) or combinations thereof. As noted, the substrate further comprises an RNase inhibitor, wherein the RNase inhibitor comprises vanadyl ribonucleoside complex (VRC), a nucleotide analogue, a commercially available RNase inhibitor (e.g., SUPERase-In™), or a triphosphate salts, such as sodium triphosphate.

In some embodiments, the substrate comprises buffer reagents in a dry-state, which may be re-hydrated during sample collection and elution. As noted, the buffer-reagents provide a pH upon hydration which stabilizes the extracted nucleic acids, wherein the hydration may be achieved by adding a sample, water or any other solution (e.g. a buffer solution).

The substrate may further comprise a chelator, an antioxidant such as a UV protectant or a free-radical scavenger or combinations thereof. Without intending to be limited to any specific UV protect, an exemplary antioxidants include, for example, hydroquinone monomethyl ether (MEHQ), hydroquinone (HQ), toluhydroquinone (THQ), uric acid, and ascorbic acid. In some embodiments, the antioxidant is THQ.

An example of a method for eluting biomolecules from a biological sample disposed on a substrate comprises contacting the biological sample to the substrate, drying the biological sample to a substantially dry state; eluting the biomolecules from the dried biological sample on the substrate by rehydrating the substrate in an elution buffer. The substrate used herein, comprises one or more monosaccharides, oligosaccharides, polysaccharides or combinations thereof on a surface of the substrate, and one or more protein denaturing agents impregnated therein the substrate under a substantially dry state.

As noted, in some embodiments, the method comprises contacting the biological sample to the saccharide coated substrate, wherein the non-limiting examples of the term "contacting" include, applying a sample to the substrate or disposing a sample to the substrate using a pipet, catheter, syringe or conduit or by using a robotic for multiple samples. The sample may be poured on the substrate manually from a tube or a vial. Contacting a biological sample comprising cells to the substrate results in cell lysis which releases nucleic acids, for example by using FTA™ Elute cellulose papers, wherein the modified FTA™ Elute cellulose papers may enable efficient elution of the nucleic acids. Nucleic acids, such as DNA or RNA may be extracted from cells disposed on the saccharide coated substrate via cell-lysis, such as by evaporative cell-lysis or cell lysis upon action of lysis reagents, for example, using impregnated lysis reagents.

As noted, in some embodiments, the method comprises drying the biological sample to a substantially dry state, wherein the term "substantially dry state" refers to drying the sample to have approximately less than 2% of water content. In one or more embodiments, the drying of the biological sample is achieved by evaporation of the liquid from the sample. In some embodiments, the biological sample is dried by desiccation of the sample. In some other embodiments, the biological sample is dried using a room temperature or elevated-temperature air-drying of the sample, which leaves the biomolecules of the biological sample intact. The drying process is selected such that the process does not affect the structure or function of the biomolecules of the biological sample.

The term "elution" refers to any method for releasing the biomolecules, such as nucleic acids from the substrate, wherein the nucleic acids are isolated from a sample. To recover preserved nucleic acids on cellulose based materials, such as 31-ETF, 903, FTA™ classic, FTA™ Elute or other substrates employed either flow through elution or punch incubation in buffers. Without ascribing to a particular hypothesis, the saccharide coating on the substrate, more specifically at the cellulosic substrate, may minimize the non-specific binding of nucleic acids to the substrate, resulting in better release of the nucleic acids during rehydration and elution of the sample.

An example of a method for eluting the stored nucleic acids from a sample comprises the steps of adding water or buffer solution onto a saccharide-coated solid substrate. In some embodiments, the elution of nucleic acids from the biological sample is achieved upon hydration of the saccharide coated solid substrate under an elevated temperature. Any method that is suitable for elution of the nucleic acids may be employed for eluting the extracted and/or stored nucleic acids from a saccharide coated solid substrate. One or more embodiments of the method comprise recovering nucleic acids from the saccharide coated substrate by solid phase extraction technique. In one or more embodiments, the nucleic acids are recovered by rehydrating the solid substrate in an aqueous solution, a buffer, or an organic solution and wherein the nucleic acids are subjected to further analysis. In one example embodiment, the nucleic acids are recovered by rehydrating the cellulose paper using an aqueous solution. In some embodiments, the nucleic acids are recovered from the solid substrate by electroelution. In some embodiments, the nucleic acids are recovered by rehydrating the cellulose paper comprising melezitose, raffinose or a combination thereof and one or more protein denaturing agents comprising thiocyanate salt, using water or a buffer.

In one or more embodiments, the term "elution buffer" refers to aqueous solutions that are commonly used for eluting nucleic acids in the art. Without intending to be limited to any specific elution buffers, the elution buffers may include water, tris(hydroxymethyl)aminomethane-ethylenediaminetetraacetic acid (Tris-EDTA or TE), 4-(2-hydroxyethyl)-1-piperazineethanesulfonic acid (HEPES), and the like. In some embodiments, the elution buffer comprises proteinase K.

The method delineated above may optionally include a step of washing the substrate before recovering the nucleic acids from the solid substrate for further analysis. For example, the substrate may be washed for one or more times with a suitable wash buffer or water prior to recovery of the nucleic acids. The washing step may remove any impurities present in the extracted and/or stored nucleic acids.

The biological sample may comprise one or more biomolecules. In one or more embodiments, the biomolecule comprises a protein, a peptide or a nucleic acid. The extracted nucleic acids comprise ribonucleic acids (RNA), deoxyribonucleic acids (DNA), peptide nucleic acids (PNA) or a combination thereof. In one embodiment, the extracted nucleic acids comprise DNA. The DNA may be genomic DNA or mtDNA. In one embodiment, the extracted nucleic acids comprise RNA. The RNA may be mRNA, tRNA, rRNA, small RNA, siRNA, miRNA, non-coding RNA, animal RNA, plant RNA, viral RNA or bacterial RNA.

The samples utilized in this method include, but are not limited to, biological samples such as blood, serum, tissue, and saliva obtained from any organism, including a human. Biological samples may be obtained by an individual undergoing a self-diagnostic test (e.g., blood glucose monitoring) or by a trained medical professional through a variety of techniques including, for example, aspirating blood using a needle or scraping or swabbing a particular area, such as a lesion on a patient's skin. Methods for collecting various biological samples are well known in the art. The term "sample" includes biological samples as defined above, but also includes, for example, tissue cultured cells and purified nucleic acids.

EXAMPLE

Reagents: 31-ETF and Ficoll PM 400 were from GE Healthcare. Guanidinium thiocyanate, trahalose, melezitose, carboxyl methyl cellulose, dextran, raffinose, alginic acid, glucosamine, chitosan, gluconic acid, amylopectin, chitosan oligosaccharide lactine, sorbitan monopalmitate, and polyvinyl alcohol were all purchased from Sigma-Aldrich (MO, USA).

Example 1

Substrates preparation—Multiple coating solutions were prepared using formulations listed in the table 1 below. 31-ETF cellulose substrates were then dipped into each of the coating solutions, forced through a nip roller, and then dried at 150° C. in an oven with air flow.

TABLE 1

| Sample | acetic acid, mg/ml | GuSCN, mg/ml | Additive, 200 mg/ml, otherwise as indicated |
|---|---|---|---|
| 4-1 | | 280 | N/A |
| 4-7 | | 280 | Decamethonium bromide, 150 mg/ml |
| 4-10 | | 280 | PVA, 5 mg/ml |
| 4-12 | | 280 | Trehalose |
| 4-13 | 20, pH 3.5 | 280 | Trehalose |
| 4-14 | | 280 | Melezitose |
| 4-15 | 20, pH 3.5 | 280 | Melezitose |
| 4-16 | | 280 | Ficoll PM 400 |
| 4-17 | | 280 | Carboxyl methyl cellulose, 20 mg/ml |
| 4-18 | | 280 | Dextran 40,000 |
| 4-19 | | 280 | Ruffinose |
| 4-20 | | 280 | Alginic acid, 20 mg/ml |
| 4-21 | | 280 | glucosamine |
| 4-22 | | 280 | chitosan, 20 mg/ml |
| 4-23 | | 280 | gluconic acid δ-lactone |
| 4-24 | | 280 | amylopectin, 20 mg/ml |
| 4-25 | | 280 | chitosan oligosacchride lactine |
| 4-26 | | 280 | glucoronic acid |
| 4-27 | | 280 | sorbitan monopalmitate, 37.5 mg/ml |

Onto each substrate prepared from Table 1, 25 µL of human whole blood (in citrate phosphate dextrose anticoagulant) was spotted onto the substrate and dried. The dried sample was then stored for 3 days at ambient temperature but low humidity (~20% RH). For two sample punches, 7 mm punch was taken from the center of dried blood spots and both punches were added to a single tube containing 230 µL TE. The punches were shaken at 900 rpm for 15 minutes at 56° C., and 200 µL of the resulting supernatant was recovered and precipitated using a DNA Extractor SP kit (Wako). The resulting DNA pellet was re-suspended in 20 µL of HET buffer (20 mM HEPES, 0.1 mM EDTA, 0.01% Tween) and DNA samples were analyzed by gel electrophoresis for qualitative analysis and the DNA concentration was measured using a PicoGreen assay.

The results of Example 1 are set forth in FIG. 1 and Table 2. FIG. 1 illustrates the change in DNA recovery from dried blood spots normalized to a control formulation (sample 4-1 of Table 1) comprising FTA Elute. Higher relative DNA recovery was observed from samples 4-14, 4-18, 4-19, and 4-21 (Table 2) comprising melezitose, dextran, raffinose, glucosamine, respectively, compared to the control formulation (sample 4-1), as shown in FIG. 1. Smaller but improved relative DNA recovery was observed from samples 4-7, 4-10, 4-16, and 4-22 comprising decamethonium bromide, PVA, Ficoll, and chitosan respectively. Little to no improvement in DNA recovery was observed in the presence of trehalose at an equivalent concentration to other types of saccharides. Concentrations of recovered DNA (as measured by a standard PicoGreen assay) are reported in Table 2.

TABLE 2

Percent recovery of DNA using various coating materials

| Sample | Recovered DNA (ng/µL) | Normalized percent change in recovery |
|---|---|---|
| 4-1 | 5.77 | 0.0% |
| 4-7 | 6.46 | 11.9% |
| 4-10 | 6.93 | 20.0% |
| 4-12 | 5.07 | −12.1% |
| 4-13 | 1.12 | −80.6% |
| 4-14 | 11.25 | 95.0% |
| 4-15 | 1.40 | −75.7% |
| 4-16 | 6.56 | 13.7% |
| 4-17 | 5.28 | −8.5% |
| 4-18 | 8.42 | 46.0% |
| 4-19 | 10.21 | 76.9% |
| 4-20 | 4.15 | −28.0% |
| 4-21 | 7.41 | 28.4% |
| 4-22 | 5.89 | 2.0% |
| 4-23 | 0.49 | −91.5% |
| 4-24 | 4.38 | −24.1% |
| 4-25 | 1.16 | −79.9% |
| 4-26 | 3.21 | −44.4% |
| 4-27 | 5.05 | −12.6% |

A portion of the recovered samples were analyzed by agarose gel electrophoresis to investigate the size and quality of the recovered DNA. As shown in FIG. 2, only high-molecular weight DNA was observed from the saccharide coated substrates that yielded increased DNA recovery, showing the "intact" or "non-degraded" form of the eluted DNA. Contrary to some of the known methods in the art, wherein recovery of DNA from a substrate may result in degraded DNA, the improved elution of DNA using the present method from a saccharide coated substrate produces high molecular weight DNA. The recovery of high molecular weight DNA implies that the method maintains the integrity of DNA molecules during storage and elution.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A saccharide coated substrate for eluting biomolecules from a biological sample, consisting essentially of:
   a cellulose membrane;
   a coating of saccharides disposed on the cellulose membrane, wherein saccharides in the coating of saccharides are selected from the group consisting of melezitose, raffinose, and a combination thereof; and
   one or more protein denaturing agents impregnated in the cellulose membrane having a water content of less than 2%,
   wherein the saccharide coated substrate is a non-water dissolvable material.

2. The saccharide coated substrate of claim 1, wherein the cellulose membrane is a porous cellulose membrane.

3. The saccharide coated substrate of claim 1, wherein the protein denaturing agents comprise salts, detergents, chaotropes, or combinations thereof.

4. The saccharide coated substrate of claim 3, wherein the protein denaturing agents are selected from thiocyanate salts.

5. The saccharide coated substrate of claim 4, wherein the protein denaturing agent is guanidinium thiocyanate.

6. The saccharide coated substrate of claim 3, wherein the protein denaturing agents are selected from the group consisting of guanidinium hydrochloride, arginine, sodium dodecyl sulfate (SDS), urea, and combinations thereof.

7. The saccharide coated substrate of claim 1, further comprising a reducing agent, a buffer, an anti-oxidant, a chelating agent, or combinations thereof.

8. The saccharide coated substrate of claim 7, wherein the reducing agent is selected from the group consisting of dithiothreitol (DTT), 2-mercaptoethanol (2-ME), tris(2-carboxyethyl)phosphine (TCEP), and combinations thereof.

9. The saccharide coated substrate of claim 7, wherein the buffer is selected from the group consisting of 2-amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers, and combinations thereof.

10. The saccharide coated substrate of claim 7, wherein the anti-oxidant is selected from the group consisting of hydroquinone monomethyl ether (MEHQ), hydroquinone (HQ), toluhydroquinone (THQ), ascorbic acid, uric acid, and combinations thereof.

11. The saccharide coated substrate of claim 7, wherein the chelating agent is selected from the group consisting of ethylenediaminetetraacetic acid (EDTA), citric acid, ethylene glycol tetraacetic acid (EGTA), and combinations thereof.

12. A method for eluting a protein, peptide or a nucleic acid from a biological sample disposed on a saccharide-coated solid substrate, consisting essentially of:
   A cellulose membrane,
   A coating of saccharides disposed on the cellulose membrane, wherein saccharides in the coating of saccharides are selected from the group consisting of melezitose, raffinose and combination thereof; and
   one or more protein denaturing agents impregnated in the cellulose membrane, drying the biological sample to a water content of less than 2%,
   contacting the biological sample to the substrate,
   eluting the protein, peptide or nucleic acid from the biological sample dried on the substrate by rehydrating the substrate in an elution buffer.

13. The method of claim 12, wherein the substrate further comprises a reducing agent, a buffer, an anti-oxidant, a chelating agent or combinations thereof impregnated therein.

14. The method of claim 12 wherein the biomolecule is DNA and the protein denaturing agent is one or more thiocyanate salts.

* * * * *